(12) United States Patent
Wong et al.

(10) Patent No.: US 6,608,107 B2
(45) Date of Patent: Aug. 19, 2003

(54) METHODS AND COMPOSITIONS TO TREAT CONDITIONS ASSOCIATED WITH NEOVASCULARIZATION

(75) Inventors: Kin-Ping Wong, Fresno, CA (US); Ming-Chung Wong, Fresno, CA (US)

(73) Assignee: Wackvom Limited, Tortola (VG)

( * ) Notice: Subject to any disclaimer, the term of this patent is extended or adjusted under 35 U.S.C. 154(b) by 0 days.

(21) Appl. No.: 10/020,526

(22) Filed: Dec. 14, 2001

(65) Prior Publication Data

US 2002/0137801 A1 Sep. 26, 2002

Related U.S. Application Data

(60) Provisional application No. 60/255,876, filed on Dec. 15, 2000.

(51) Int. Cl.[7] ............................................. A61K 31/225
(52) U.S. Cl. ...................... 514/548; 514/682; 514/700
(58) Field of Search ................................ 514/548, 682, 514/700

(56) References Cited

U.S. PATENT DOCUMENTS

| | | | | |
|---|---|---|---|---|
| 5,026,726 A | * | 6/1991 | Jagt et al. | 514/468 |
| 5,260,327 A | * | 11/1993 | Kim et al. | 514/405 |
| 5,385,936 A | * | 1/1995 | Flack et al. | 514/548 |
| 5,780,675 A | * | 7/1998 | Royer et al. | 562/467 |
| 5,936,120 A | * | 8/1999 | Royer et al. | 562/461 |
| 6,114,397 A | * | 9/2000 | Flack et al. | 514/682 |

OTHER PUBLICATIONS

Benz et al, Life Science, vol. 49, pp. pl67–pl72, 1991.*
International Search Report dated Jul. 18, 2002.
Dao, V.–T. et al. "Synthesis and cytotoxicity of gossypol related compounds" *Eur. J. Med. Chem.* (Sep. 2000) 35(9):805–813.
Jan, C.–R. et al. "Novel effects of gossypol, a chemical contraceptive in man: mobilzation of internation $Ca^{2+}$ and activation of external $Ca^{2+}$ entry in intact cells" *Biochimica et Biophysica Acta* (Apr. 2000) 1496(2–3):270–276.
Benz, C.C., et al. "Gossypol Effects on Endothelial Cells and Tumor Blood Flow", *Life Sciences*, (1991) 49: PL–67–PL–72.

* cited by examiner

*Primary Examiner*—James H Reamer

(57) ABSTRACT

This invention also provides a method to inhibit neovascularization in tissue by delivering to the cell or tissue an effective amount of gossypol, or a pharmaceutically acceptable salt, derivative or prodrug thereof. Also provided herein is a method for treating a disease associated with hyproliferation of endothelial cells and/or neovascularization by administering to a subject an effective amount of gossypol, or a pharmaceutically acceptable salt, derivative or prodrug thereof. Kits to treat patients are provided as well.

41 Claims, 1 Drawing Sheet

METHODS AND COMPOSITIONS TO TREAT CONDITIONS ASSOCIATED WITH NEOVASCULARIZATION

CROSS-REFERENCE TO RELATED APPLICATIONS

This application claims the benefit under 35 U.S.C. § 119(e) of U.S. Provisional Application No. 60/255,876, filed Dec. 15, 2000, the contents of which are hereby incorporated by reference into the present disclosure.

FIELD OF THE INVENTION

The present invention is in the field of pharmaceuticals. In particular, it is related to the field of anti-angiogenic pharmaceuticals for the prevention and treatment of disease.

BACKGROUND

Angiogenesis is the process through which new vascular structures arise by outgrowth from pre-existing capillaries. In this process, endothelial cells become detached from the basement membrane as this support is degraded by proteolytic enzymes. These cells then migrate out from the parent vessel, divide, and form into a newly differentiated vascular structure (Risau, (1997) Nature 386:671–674; Wilting et al., (1995) Cell. Mol. Biol. Res. 41(4):219–232). A variety of different biological factors have been found to function in controlling blood vessel formation (Bussolino et al., (1997) Trends in Biochem Sci 22(7):251–256; Folkman and D'Amore, (1996) Cell 87:1153–1155). These include proteins with diverse functions such as growth factors, cell surface receptors, proteases, protease inhibitors, and extracellular matrix proteins (Achen and Stacker, (1998) Int. J. Exp. Pathol. 79:255–265; Devalaraja and Richmond, (1999) Trends in Pharmacol. Sci. 20(4):151–156; Hanahan, (1997) Science 277:48–50; Maisonpierre et al, (1997) Science 277:55–60; Suri et al, (1996) Cell 87:1171–1180; Sato et al, (1995) Nature 376:70–74; Mignatti and Rifkin, (1996) Enzyme Protein 49:117–137; Pintucci et al., (1996) Semin Thromb Hemost 22(6)517–524; Vernon and Sage, (1995) Am. J. Pathol. 147(4):873–883; Brooks et al., (1994) Science 264:569–571; Koch et al., (1995) Nature 376:517–519). The complexity of the angiogenic process and the diversity of the factors that control its progression provide a useful array of points for therapeutic intervention to control vascular formation in vivo.

Angiogenesis normally occurs in a carefully controlled manner during embryonic development, during growth, and in special cases such as wound healing and the female reproductive cycle (Wilting and Christ, (1996) Naturwissenschaften 83:153–164; Goodger and Rogers, (1995) Microcirculation 2:329–343; Augustin et al., (1995) Am. J. Pathol. 147(2):339–351). Some of the important steps in the process of angiogenesis are: 1) growth factor (i.e. vascular endothelial growth factor, VEGF) signaling; 2) matrix metalloproteinases (MMP) and VEGF receptor interaction; 3) endothelial cell migration to site of growth factor signaling; and 4) endothelial cell tubule formation. Pathological angiogenesis play a central role in a number of human diseases including tumor growth and metastatic cancer, diabetic retinopathy, rheumatoid arthritis, and other inflammatory diseases such as psoriasis (Folkman, (1995) Nature Med. 1(1):27–31; Polverini, (1995) Rheumatology 38(2): 103–112; Healy et al., (1998) Hum. Reprod. Update 4(5): 736–396). In these cases, progression of disease is driven by persistent unregulated angiogenesis. For example, in rheumatoid arthritis, new capillary blood vessels invade the joints and destroy the cartilage. In diabetic retinopathy, capillaries in the retina invade the vitreous, bleed and cause blindness. In diabetic retinopathy, capillaries in the retina invade the vitreous, bleed and cause blindness. Significantly, tumor growth and metastisis are angiogenesis dependent. Most primary solid tumors go through a prolonged avascular state during which growth is limited to approximately 1–2 mm in diameter. Up to this size, tumor cells can obtain the necessary oxygen and nutrient supply by passive diffusion. These microscopic tumor masses can eventually switch on angiogenesis and recruit surrounding blood vessels to begin sprouting capillaries that vascularize the tumor mass, providing the potential for continuing expansion of the tumor and metastasis of malignant cells to distant locations. Although significant progress has been made in understanding the biological events that occur during pathological angiogenesis, there are presently no effective pharmaceutical compounds that are useful for controlling angiogensis in vivo. Thus, effective therapies capable of controlling angiogenesis have the potential to alleviate a significant number of human diseases.

Traditionally, pharmaceutical compounds have been developed by screening synthetic chemical compounds for desirable pharmaceutical properties and then testing them for toxicity and effectiveness in vivo. Compounds selected this way frequently have toxic side effects in vivo and this approach has not been successful in developing effective angiogensis inhibitors for disease therapy. More recently, techniques of molecular biology have been applied to develop angiogenesis inhibitors. Protein inhibitors of angiogenesis such as angiostatin (O'Reilly et al., (1994) Cell 79(2):315–328) and endostatin (O'Reilly et al., (1997) Cell 88(2):277–285), that control vascular formation in experimental models, have been discovered. Nevertheless, such protein therapeutics are expensive to produce and have been found to be difficult to formulate and deliver in subjects. At present, protein angiogensis inhibitors have yet to be developed into therapeutic pharmaceuticals for disease patients. Thus, there exists a need for therapeutic compounds that can be safely administered to a patient and be effective at inhibiting the pathological growth of vascular endothelial cells. The present invention provides compositions and methods that are useful for this purpose and provides related advantages as well.

DISCLOSURE OF THE INVENTION

Gossypol and its derivatives have been found to inhibit growth and proliferation of endothelial cells and the process of vascularization. Thus, this invention provides methods for inhibiting the proliferation of endothelial cells, and in particular cells that are dividing to a pathological degree or in a tissue. This invention also provides a method to inhibit neovascularization in tissue. Each method requires delivering to the cell or tissue an effective amount of gossypol, or a pharmaceutically acceptable salt, derivative or prodrug thereof.

Also provided herein is a method for treating a disease associated with hyperproliferation of endothelial cells and/or neovascularization by administering to a subject an effective amount of gossypol, or a pharmaceutically acceptable salt, derivative or prodrug thereof. Kits to treat patients are provided as well.

Further provided is a screen for identifying new therapeutic agents that have the same, similar or better therapeutic effect as gossypol, or a pharmaceutically acceptable salt, derivative or prodrug thereof. The screen requires comparing the antiproliferative effect of gossypol, or a pharmaceutically acceptable salt, derivative or prodrug thereof, with the agent.

MODES FOR CARRYING OUT THE INVENTION

Figure 1:
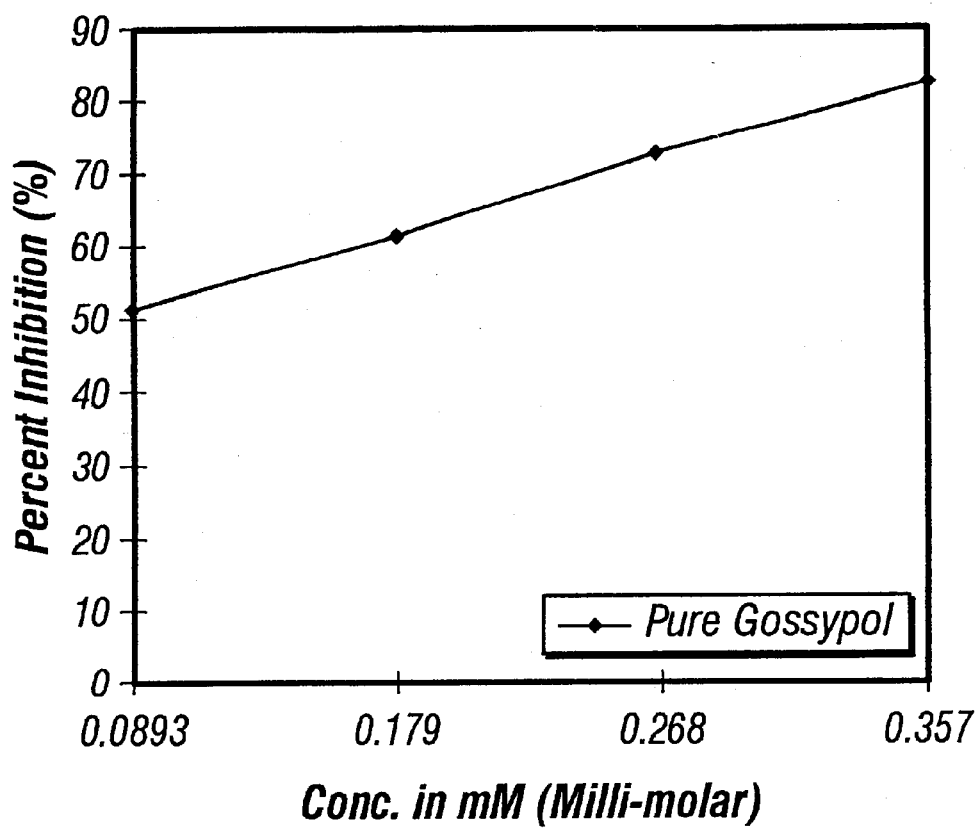
FIG. 1 is a graph showing percent inhibition of pure gossypol in the Endothelial Cell Assay.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

The practice of the present invention employs, unless otherwise indicated, conventional techniques of molecular biology (including recombinant techniques), microbiology, cell biology, biochemistry and immunology, which are within the skill of the art. Such techniques are explained fully in the literature.

Definitions

As used herein, certain terms may have the following defined meanings.

As used in the specification and claims, the singular form "a," "an" and "the" include plural references unless the context clearly dictates otherwise. For example, the term "a cell" includes a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are well known in the art.

The term "isolated" means separated from constituents, cellular and otherwise, in which the compound is normally associated with in nature.

A "subject" or "host" is a vertebrate, preferably an animal or mammal, more preferably a human patient. Mammals include, but are not limited to, murines, simians, human patients, farm animals, sport animals, and pets.

The terms "cancer," "neoplasm," and "tumor," used interchangeably and in either the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but also any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by such procedures as CAT scan, magnetic resonance imaging (MRI), X-ray, ultrasound or palpation. Biochemical or immunologic findings alone may be insufficient to meet this definition.

As used herein, "inhibit" means to stop, delay or slow the growth, proliferation or cell division of endothelial cells or the formation of blood vessels in tissue. Methods to monitor inhibition include, but are not limited to endothelial cell proliferation assays, measurement of the volume of a vascular bed by determination of blood content and quantitative determination of the density of vascular structures. When the culture is a mixture of cells, neovascularization is monitored by quantitative measurement of cells expressing endothelial cell specific markers such as angiogenic factors, proteolytic enzymes and endothelial cell specific cell adhesion molecules.

A "composition" is intended to mean a combination of active agent and another compound or composition, inert (for example, a detectable agent or label) or active, such as an adjuvant.

A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin, REMINGTON'S PHARM. SD., 15TH ED. (Mack Publ. Co., Easton (1975)).

An "effective amount" is an amount sufficient to effect beneficial or desired results. For example, a therapeutic amount is one that achieves the desired therapeutic effect. This amount may be the same or different from a prophylatically effective amount, which is an amount necessary to prevent onset of disease or disease symptoms. An effective amount can be administered in one or more administrations, applications or dosages.

Gossypol, a phenolic aldehyde, is naturally present as a yellow pigment in the genus Gossypium, commonly known as cotton. It has been shown to cause degeneration of many accessory organs by altering steroid biosynthesis in the reproductive system in a manner resembling castration. However, gossypol has recently stimulated interest as a potential anti-cancer agent for steroid responsive tumors (e.g., Lin, et al. (1995) Proc. Ann. Mtg. Am. Assoc. Cancer Res. 36:A2329). It is thought that gossypol exerts its inhibitory effect in cell growth via a mechanism distal to its effect on the steroidogenesis pathway.

The inventors have discovered that gossypol inhibits endothelial cell growth and possesses anti-angiogenic properties. In accordance with these findings, this invention provides a method for inhibiting the growth of endothelial cells by delivering to the cells a growth inhibitory amount of gossypol, or a pharmaceutically acceptable derivative, salt or prodrug thereof. This invention also provides a method of inhibiting vascularization in a tissue by delivering to the tissue an anti-vascularization amount of gossypol, or a pharmaceutically acceptable derivative, salt or prodrug thereof.

This method can be practiced in vitro or in vivo. When practiced in vitro, endothelial cells or vascularized tissue are cultured under conditions well known to skill in the art, e.g., as exemplified below. The cells and/or tissue can be from an established cell line or cultured from a biopsy sample obtained from a subject. Gossypol or a pharmaceutically acceptable derivative, salt or prodrug thereof is then directed added to the culture medium or delivered as a component of a pharmaceutical composition.

In one aspect the derivative of gossypol is gossypol acetate. As used herein, the term "gossypol" is intended to encompasses various separate embodiments unless specifically noted otherwise. The term encompasses the racemate, and its purified enantiomeric forms (±) and (−), derivatives such as gossypol acetate, pharmaceutically acceptable salts and prodrugs thereof. Purification of racemic gossypol is described below. In one aspect, the purified gossypol is the (−) form only. In a further aspect, it is the (+) form only. The racemic, (+) or (−) forms are each commercially available and methods to isolate each are known in the art. For example, using HPLC chiral columns such as CHIRAL-AGP, CHIRAL-CBH and CHIRAL-HAS, are available from Chrom Tech International, AB. Perkins-Elmer also sells a chiral separation kit under Sulfadex Chiral Separation Kit.

Examples of salts include: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylproprionate, picrate, pivalate, propionate, succinate, tartrate, thiocyanate, tosylate and undecanoate. Other examples of salts include anions of the compounds of the present invention compounded with a suitable cation such as $Na^+$, $NH_4^+$, and $NW_4^+$ (wherein W is a $C_{14}$ alkyl group).

For therapeutic use, salts of the compounds of the present invention will be pharmaceutically acceptable. However, salts of acids and bases which are non-pharmaceutically acceptable may also find use, for example, in the preparation or purification of a pharmaceutically acceptable compound.

Not every therapy is effective for each individual and therefore, an in vitro assay to gauge efficacy for each patient would be advantageous. The present method provides these means to determine whether gossypol therapy will treat an individual's subject's specific disease related to pathological proliferation of endothelial cells. Examples of such are provided herein. For example, a tissue biopsy is isolated from the patient and contacted with an effective amount of a pharmaceutical composition or therapy as defined herein and under conditions effective for growth and proliferation of the cells. Inhibition of growth of the pathological cells as determined by conventional procedures, e.g., the CPAE assay described herein, indicates that the inventive compositions and/or therapies may effectively treat the patient.

Angiogenesis or the formation of new vasculature is a fundamental process by which new blood vessels are formed. It participates in essential physiological events, such as reproduction development and wound healing. Under normal conditions, angiogenesis is highly regulated. However, many diseases are driven by persistent unregulated angiogenesis. In rheumatoid arthritis, new capillary blood vessels invade the joints and destroy the cartilage. In diabetic retinopathy, new capillaries in the retina invade the vitreous, bleed, and cause blindness. Tumor growth and metastasis are angiogenesis-dependent. Most primary solid tumors go through a prolonged state of avascular, and apparently dormant, growth in which the maximum size attainable is ~1–2 mm in diameter. Up to this size, tumor cells can obtain the necessary oxygen and nutrient by simple passive diffusion. These microscopic tumor masses can eventually switch on angiogenesis by recruiting surrounding mature host blood vessels to begin sprouting new blood vessel capillaries which grow toward, and eventually infiltrate the tumor mass, thus setting in motion the potential for relentless expansion of tumor mass and hematogenous metastatic spread as well. The angiogenic switch was initially hypothesized to be triggered by the ectopic production and elaboration by tumor cells of a growth factor called "tumor angiogenesis factor" (TAF).

This invention also provides a method of treating a disorder associated with pathological neovascularization in a subject by administering to the subject a therapeutically effective amount of gossypol (racemate, (+) or (−)), or a pharmaceutical composition containing one or more of these. As used in this context, to "treat" means to alleviate the symptoms associated with pathological neovascularization as well as the reduction of neovascularization. Such conditions include, but are not limited to arthritic conditions, neovascular-based dermatological conditions, diabetic retinopathy, karposi's sarcoma, age-related macular degeneration, telangectasia, glaucoma, keloids, corneal graft rejection, wound granularization, angiofibroma, Osler-Webber Syndrome, myocardial angiogenesis, and scleroderma. Exemplary arthritic conditions are selected from the group consisting of rheumatoid arthritis and osteoarthritis. For the treatment of cancers and solid tumors, to "treat" includes inhibition of the growth of blood vessels resulting in a lack of nutrients for the tumors and/or cancer cells needed by the tumor for its growth. Tumors and growths will decrease in size and possibly disappear. Administration for the treatment of arthritic conditions will result in decreased blood vessel formation in cartilage, specifically joints, resulting in increased mobility and flexibility in these regions. For the treatment of psoriasis, administration will reduce dermatological symptoms such as scabbing, flaking and visible blood vessels under the surface of the skin. In diabetic retinopathy, administration of the active fraction will reduce the formation of extraneous blood vessels in the retina, resulting in unobstructed vision. In the treatment of Kaposi's Sarcoma, administration of the active fraction will inhibit the growth and/or further formation of blood vessels, thereby inhibiting the formation of lesions and/or tumors that arise.

Applicants have unexpectedly discovered that that (−) gossypol concentrates in the major organs such as the heart, spleen and muscles. Thus, in one aspect, this invention provides a means to treat or alleviate the symptoms of neovascularization in these organs by delivering an effective amount of (−) gossypol to the subject or cells of the organ of interest. The (+) form concentrates in the kidneys. Thus, in another aspect, this invention provides a means to treat or alleviate the symptoms of neovascularization in the kidney by delivering an effective amount of (+) gossypol to the subject or kidney cells.

When the active fraction is administered to a subject such as a mouse, a rat or a human patient, the agent can be added to a pharmaceutically acceptable carrier and systemically, orally, transdermally or topically administered to the subject. Therapeutic amounts can be empirically determined and will vary with the pathology being treated, the subject being treated and the toxicity of the form of the fraction used in the therapeutic method. The active fraction can be delivered orally, intravenously, intraperitoneally, or transdermally. When delivered to an animal, the method is useful to further confirm efficacy of the active fraction.

As an example of an animal model, groups of nude mice (Balb/c NCR nu/nu female, Simonsen, Gilroy, Calif.) are each subcutaneously inoculated with about $10^5$ to about $10^9$ hyperproliferative cells as defined herein. When the graft is established, the compound is administered, for example, by subcutaneous injection around the graft. Measurements to determine reduction of graft size are made in two dimensions using venier calipers twice a week.

The MRL/lpr mice (MRL/MpJ-Fas$^{lpr}$) from Jackson Labs (Maine) are useful to test or monitor efficacy in arthritic conditions. A positive therapeutic benefit includes reduced swelling of the joints and hindlegs of animals and reduced cartilage degradation that can be monitored by X-ray.

Administration in vivo can be effected in one dose, multiple doses, continuously or intermittently throughout the course of treatment. Methods of determining the most effective means and dosage of administration are well known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents can be found below.

The compositions and pharmaceutical formulations of the present invention can be used in the manufacture of medicaments and health food supplements and for the treatment of humans and other animals by administration in accordance with conventional procedures, such as an active ingredient in pharmaceutical compositions.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition to a compound of the present invention, the pharmaceutical compositions can also contain other pharmaceutically active ingredients.

More particularly, the active fraction also referred to herein as the active ingredient, may be administered for therapy by any suitable route including oral, rectal, nasal, topical (including transdermal, aerosol, buccal and sublingual), vaginal, parental (including subcutaneous, intramuscular, intravenous and intradermal) and pulmonary. It will also be appreciated that the preferred route will vary with the condition and age of the recipient, and the disease being treated.

When the method is practiced in vivo, pathological endothelial cell growth or neovascularization is inhibited in a subject. A therapeutically effective amount of gossypol, (racemate, (+) or (−)), or a pharmaceutically acceptable derivative, salt or prodrug thereof is delivered to the subject in an amount effective to derive its intended result. This invention also provides a method of treating a disorder associated with pathological neovascularization in a subject by administering to the subject a therapeutically effective amount or a growth inhibitory amount of gossypol (racemate, (+) or (−)), or a pharmaceutically acceptable derivative, salt or prodrug thereof Such conditions include, but are not limited to arthritic conditions, neovascular-based dermatological conditions, diabetic retinopathy, restenosis, Karposi's Sarcoma, age-related macular degeneration, telangectasia, glaucoma, keloids, corneal graft rejection, wound granularization, angiofibroma, Osler-Webber Syndrome, myocardial angiogenesis and scleroderma. Exemplary arthritic conditions are selected from the group consisting of rheumatoid arthritis, psoriatic arthritis and osteoarthritis.

When gossypol is administered to a subject such as a mouse, a rat or a human patient, the agent can be added to a pharmaceutically acceptable carrier and systemically, orally, transdermally or topically administered to the subject. Therapeutic amounts can be empirically determined and will vary with the pathology being treated, the subject being treated and the condition to be treated.

Not every therapy is effective for each individual and therefore, an in vitro assay to gauge efficacy for each patient would be advantageous. The present method provides these means to determine whether compositions or therapies will treat a subject's specific disease related to pathological proliferation of endothelial cells or vascularization. For example, a tissue biopsy is isolated from the patient and contacted with an effective amount of a pharmaceutical composition or therapy as defined herein and under conditions effective for growth and proliferation of the cells. Inhibition of growth of the pathological cells as determined by conventional procedures, e.g., the CPAE assay described herein, indicates that the inventive compositions and/or therapies may effectively treat the patient.

While it is possible for the drug ingredient to be administered alone, it is preferable to present it as a pharmaceutical formulation comprising at least one active ingredient, as defined above, together with one or more pharmaceutically acceptable carriers therefor and optionally other therapeutic agents. Each carrier must be "acceptable" in the sense of being compatible with the other ingredients of the formulation and not injurious to the patient.

Formulations include those suitable for oral, rectal, nasal, topical (including transdermal, buccal and sublingual), vaginal, parenteral (including subcutaneous, intramuscular, intravenous and intradermal) and pulmonary administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations of the present invention suitable for oral administration may be presented as discrete units such as capsules, cachets or tablets, each containing a predetermined amount of the active ingredient; as a powder or granules; as a solution or suspension in an aqueous or non-aqueous liquid; or as an oil-in-water liquid emulsion or a water-in-oil liquid emulsion. The active ingredient may also be presented a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention may be formulated as an ointment, cream, suspension, lotion, powder, solution, past, gel, spray, aerosol or oil. Alternatively, a formulation may comprise a patch or a dressing such as a bandage or adhesive plaster impregnated with active ingredients and optionally one or more excipients or diluents.

For diseases of the eye or other external tissues, e.g., mouth and skin, the formulations are preferably applied as a topical ointment or cream containing the active ingredient. When formulated in an ointment, the drug may be employed with either a paraffinic or a water miscible ointment base. Alternatively, the drug ingredients may be formulated in a cream with an oil-in-water cream base.

If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof The topical formulations may desirably include a compound which enhances absorption or penetration of the drug ingredient through the skin or other affected areas. Examples of such dermal penetration enhancers include dimethylsulfoxide and related analogues.

The oily phase of the emulsions of this invention may be constituted from known ingredients in any known manner. While this phase may comprise merely an emulsifier (otherwise known as an emulgent), it desirably comprises a mixture of at lease one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulphate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the prodrug ingredient, such carriers as are known in the art to be appropriate.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the prodrug ingredient.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of a drug ingredient.

It should be understood that in addition to the ingredients particularly mentioned above, the formulations of this invention may include other agents conventional in the art having regard to the type of formulation in question, for example, those suitable of oral administration may include such further agents as sweeteners, thickeners and flavoring agents. They may also contain additional active agents, e.g., anti-tumor, anti-cancer, anti-angiogenic or immune enhancers.

Gossypol, (the racemate or an optically pure composition) its prodrug, salt or derivative thereof and compositions of the same may also be presented for the use in the form of veterinary formulations, which may be prepared, for example, by methods that are conventional in the art.

This invention further provides a method for screening for a therapeutic agent for inhibiting neovascularization or endothelial cell growth. The screen comprises:

(a) contacting the agent with a suitable cell or tissue sample;

(b) contacting a separate sample of the suitable cell or tissue sample with a therapeutically effective amount of gossypol or a pharmaceutically acceptable derivative, salt or prodrug thereof and (c) comparing the growth of the sample of step (a) with the growth of the sample of step (b), and wherein any agent of step (a) that inhibits the growth to the same or similar extent as the sample of step (b) is a therapeutic agent for inhibiting neovascularization or the growth of endothelial cells.

Additional therapies and agents as described herein may optionally be combined with the samples.

A kit for treating a disorder associated with pathological neovascularization in a subject, also is provided by this invention. The kit includes a therapeutically effective amount of gossypol (racemate, (+) or (−)), or a pharmaceutically acceptable derivative, salt or prodrug thereof and instructions for use. The kit is useful to treat disorders selected from the group consisting of arthritic conditions, neovascular-based dermatological conditions, diabetic retinopathy, restinosis, Karposi's Sarcoma, age-related macular degeneration, telangectasia, glaucoma, keloids, corneal graft rejection, wound granularization, angiofibroma, Osler-Webber Syndrome, myocardial angiogenesis, scleroderma, rheumatoid arthritis, psoriatic arthritis and osteoarthritis.

The following examples are intended to illustrate, but not limit the invention.

EXAMPLES

Example 1

Isolation and Purification of Gossypol

Gossypol and gossypol acetates are prepared according to Hron and coworkers (Hron, R. J., Sr. et al (1987) J. Am Oil Chem Soc. 64:1315; Hron, R. J., Sr. et al (1992) U.S. Pat. No. 5,112,637; Hron, R. J., Sr. et al (1992) J. Am. Chem Soc. 69:950) and Kuk and coworkers (Kuk, M. S., et al (1992) U.S. Pat. No. 5,077,441; Kuk, M. S. et al (1993) J. Am. Oil Chem Soc. 70:209; Kuk, M. S. et al (1994) J Am. Oil Chem Soc. 71:417). Some samples are generous gifts of Dr. M. C. Calhoun of the Texas Agriculture Experimental Station, Texas A & M University, San Angelo, Tex.

Example 2

Inhibition of Endothelial Cell Assay by Gossypol

Endothelial Cell Assays:

The assays were carried out according to the procedures of Connally, et al. (1986) Anal. Biochem. 152:136–4 with modifications (Liang and Wong (1999) ANGIOGENESIS: FROM THE MOLECULAR TO INTEGRATIVE PHARMACOLOGY edited by Maradoudakis, Kluwer Academic/Plenum. Publishers, New York).

Results and Discussion:

TABLE I

Inhibition of Endothelial Cell Assay by Gossypol

| Sample | Control (EtOH) | Concentration of Gossypol: 25 mM | Gossypol Acetate | Gossypol Acetate |
|---|---|---|---|---|
| 1 | 0.2841 | 0.0057 | 0.0588 | 0.3065 |
| 2 | 0.2625 | 0.0068 | 0.2273 | 0.3035 |
| 3 | 0.2699 | 0.0076 | 0.3638 | 0.3269 |
| 4 | 0.3569 | 0.0112 | 0.4150 | 0.3289 |
| 5 | 0.2934 | 0.0078 | 0.2166 | 0.3165 |
| Inhibition: | 10.5% | 97.6% | 46.2% | 21.3% |

The results of our endothelial cell culture assays are shown in Table I, above. Pure gossypol does inhibit cell growth. The results of the endothelial cell assay show that the addition of gossypol to the endothelial cell assay proves significant inhibition of endothelial cell growth. In the assay, a pure gossypol sample elicited a 97.6% inhibition rate of endothelial cell growth. The sample from gossypol acetate, a stable derivative of gossypol, also showed significant inhibition in the range of 21.3 to 46.2% inhibition dependent upon concentrations. This is a strong indication that gossypol is an extremely effective endothelial cell growth inhibitor. The control only accounted for 10% of inhibition.

Figure 2:
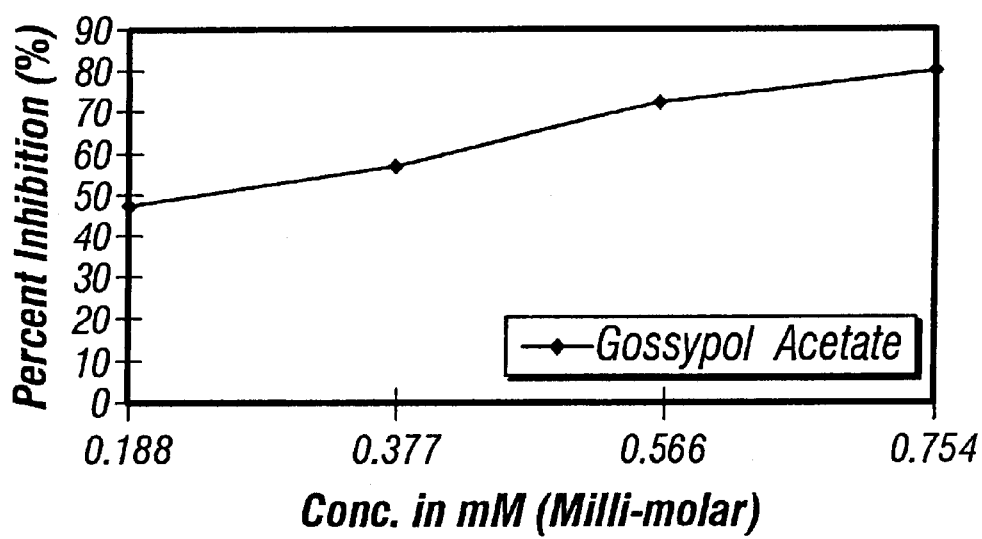
FIG. 2 is a graph showing the cell inhibitory effects of gossypol acetate in the Endothelial Cell Assay.

A concentration-dependence study on the inhibition of angiogenesis was also performed and shown in FIG. 1 for pure gossypol and FIG. 2 for gossypol acetate. It is clear that even at very low concentrations (fractions of milimolar), gossypol is a very strong inhibitor of endothelial cell growth.

Although the foregoing invention has been described in some detail by way of illustration and example for purposes of clarity of understanding, it will be apparent to those skilled in the art that certain changes and modifications will be practiced. For example, as is apparent to those of skill in the art, the invention method can be combined with one or more known anti-tumor, anti-angiogenic or immune enhancing therapies and compositions, e.g., shark cartilage, tyrosphingosine or sphingosine. Therefore, the description and examples should not be construed as limiting the scope of the invention, which is delineated by the appended claims.

What is claimed is:

1. A method for inhibiting the growth of endothelial cells, comprising delivering to the cells a growth inhibitory amount of gossypol, or a pharmaceutically acceptable derivative, salt or prodrug thereof.

2. The method of claim 1, wherein the gossypol is selected from the group consisting of (+) gossypol, (−) gossypol and the racemate.

3. The method of claim 1, wherein the derivative of gossypol is a gossypol acetate.

4. A method of inhibiting vascularization in a tissue, comprising delivering to the tissue an anti-vascularization amount of gossypol, or a pharmaceutically acceptable derivative, salt or prodrug thereof.

5. The method of claim 4, wherein the gossypol is selected from the group consisting of (+) gossypol, (−) gossypol and the racemate.

6. The method of claim 4, wherein the derivative of gossypol is a gossypol acetate.

7. A method of inhibiting vascularization in a major organ, comprising delivering to the tissue an anti-vascularization amount of (−) gossypol, or a pharmaceutically acceptable derivative, salt or prodrug thereof.

8. The method of claim 7, wherein the major organ is selected from the group consisting of heart, spleen, and muscles.

9. A method of inhibiting vascularization in kidney cells or tissue, comprising delivering to the tissue an anti-vascularization amount of (+) gossypol, or a pharmaceutically acceptable derivative, salt or prodrug thereof.

10. The method of any one of claims 1, 4, 7 or 9, wherein the delivering is in vitro or in vivo.

11. The method of claim 10, further comprising delivering an effective amount of an agent or therapy selected from the group consisting of anti-angiogenic, anti-tumor, and immune enhancing.

12. A method of treating a disorder associated with pathological neovascularization in a host, comprising administering to a subject a therapeutically effective amount of growth inhibitory amount of gossypol, or a pharmaceutically acceptable derivative, salt or prodrug thereof.

13. The method of claim 12, wherein the gossypol is selected from the group consisting of (+) gossypol, (−) gossypol and the racemate.

14. The method of claim 12, further comprising administering to the subject an effective amount of an agent or therapy selected from the group consisting of anti-angiogenic, anti-tumor and immune enhancing.

15. The method of claim 12, wherein the disorder is selected from the group consisting of arthritic conditions, neovascular-based dermatological conditions, diabetic retinopathy, Karposi's Sarcoma, age-related macular degeneration, restenosis, telangectasia, glaucoma, keloids, corneal graft rejection, wound granularization, angiofibroma, Osler-Webber Syndrome, myocardial angiogenesis, psoriatic arthritis and scleroderma.

16. The method of claim 15, wherein the disorder is an arthritic condition selected from the group consisting of rheumatoid arthritis, psoriatic arthritis and osteoarthritis.

17. The method of claim 12, wherein the derivative of gossypol is a gossypol acetate.

18. A method of treating a disorder associated with pathological neovascularization in a major organ in a subject, comprising administering to the subject a therapeutically effective amount of (−) gossypol, or a pharmaceutically acceptable derivative, salt or prodrug thereof.

19. The method of claim 18, wherein the major organ is selected from the group consisting of heart, spleen, and muscles.

20. The method of claim 18, further comprising administering to the subject an effective amount of an agent or therapy selected from the group consisting of anti-angiogenic, anti-tumor and immune enhancing.

21. A method of treating a disorder associated with pathological neovascularization in the kidney of a subject, comprising administering to the subject a therapeutically effective amount of (+) gossypol, or a pharmaceutically acceptable derivative, salt or prodrug thereof.

22. The method of any one of claims 9, 12, 15 or 18 wherein the delivering is by oral administration, intravenous, intraperitoneal, or transdermal.

23. The method of claim 21, further comprising administering to the subject an effective amount of an agent or therapy selected from the group consisting of anti-angiogenic, anti-tumor and immune enhancing.

24. The method of claim 21, wherein the host or subject is an animal.

25. The method of claim 24, wherein the animal is selected from the group consisting of a pet, a farm animal or a human patient.

26. A method for improving the general health and well being of a subject comprising administering to the subject an effective amount of gossypol.

27. The method of claim 26 wherein the amount is delivered as a health food supplement.

28. The method of claim 26, wherein the host or subject is an animal.

29. The method of claim 26, wherein the animal is selected from the group consisting of a pet, a farm animal or a human patient.

30. The method of claim 26, wherein the gossypol is selected from the group consisting of (+) gossypol, (−) gossypol and the racemate.

31. The method of claim 26, wherein the derivative of gossypol is a gossypol acetate.

32. A method for screening for a therapeutic agent for inhibiting neovascularization or endothelial cell growth comprising the steps of:

a. contacting the agent with a suitable cell or tissue sample;

b. contacting a separate sample of the suitable cell or tissue sample with a therapeutically effective amount of gossypol or a pharmaceutically acceptable derivative, salt or prodrug thereof; and c. comparing the growth of the sample of step (a) with the growth of the sample of step (b), and wherein any agent of step (a) that inhibits the growth to the same or similar extent as the sample of step (b) is a therapeutic agent for inhibiting neovascularization or the growth of endothelial cells.

33. The method of claim 32, wherein the contacting is in vitro or in vivo.

34. The method of claim 32, wherein the gossypol is selected from the group consisting of (+) gossypol, (−) gossypol and the racemate.

35. The method of claim 32, wherein the derivative of gossypol is a gossypol acetate.

36. The method of claim 32, further comprising contacting the samples of steps a and b with an effective amount of an agent or therapy selected from the group consisting of anti-angiogenic, anti-tumor or immune enhancing.

37. A kit for treating a disorder associated with pathological neovascularization in a subject, comprising a therapeutically effective amount of gossypol, or a pharmaceutically acceptable derivative, salt or prodrug thereof and instructions for use.

38. The kit of claim 37, wherein the disorder is selected from the group consisting of arthritic conditions, neovascular-based dermatological conditions, diabetic retinopathy, Karposi's Sarcoma, age-related macular degeneration, restenosis, telangectasia, glaucoma, keloids, corneal graft rejection, wound granularization, angiofibroma, Osler-Webber Syndrome, myocardial angiogenesis, and scleroderma.

39. The kit of claim 38, wherein the disorder is an arthritic condition selected from the group consisting of rheumatoid arthritis, psoriatic arthritis and osteoarthritis.

40. The kit of claim 37, wherein the gossypol is selected from the group consisting of (+) gossypol, (−) gossypol and the racemate.

41. The kit of claim 37, wherein the derivative of gossypol is a gossypol acetate.

* * * * *